US012584102B2

(12) United States Patent
Fan et al.

(10) Patent No.: US 12,584,102 B2
(45) Date of Patent: Mar. 24, 2026

(54) OCEANOBACILLUS JEDDAHENSE STRAIN HMF12 AND ITS APPLICATION

(71) Applicant: GUO YANG INT'L MICROBIOLOGY GROUP, New Beach, CA (US)

(72) Inventors: Yafei Fan, New Beach, CA (US); Gen Song, New Beach, CA (US); Chunguang Song, New Beach, CA (US); Xiufen Zhang, New Beach, CA (US); Shujian Zhang, New Beach, CA (US); Yanmin Zhao, New Beach, CA (US); Zhenhua Jia, New Beach, CA (US); Yingchao Zhang, New Beach, CA (US); Yali Huang, New Beach, CA (US); Xiaolin Zhang, New Beach, CA (US); Xiangyong Luo, New Beach, CA (US); Hong Shen, New Beach, CA (US); Qiong Song, New Beach, CA (US); Zhigang Zhao, New Beach, CA (US); Jirong Cui, New Beach, CA (US); Yanhong Wu, New Beach, CA (US); Lili Han, New Beach, CA (US); Jie Chen, New Beach, CA (US); Long Li, New Beach, CA (US); Xia Li, New Beach, CA (US)

( * ) Notice: Subject to any disclaimer, the term of this patent is extended or adjusted under 35 U.S.C. 154(b) by 0 days.

(21) Appl. No.: 19/256,777

(22) Filed: Jul. 1, 2025

(65) Prior Publication Data

US 2026/0035660 A1 Feb. 5, 2026

(30) Foreign Application Priority Data

Jul. 31, 2024 (CN) .......................... 202411036705.9

(51) Int. Cl.
*C12N 1/20* (2006.01)
*A01P 3/00* (2006.01)
*C12N 1/205* (2026.01)
*C12R 1/01* (2006.01)

(52) U.S. Cl.
CPC ............... *C12N 1/205* (2021.05); *A01P 3/00* (2021.08); *C12R 2001/01* (2021.05)

(58) Field of Classification Search
CPC ... A01P 1/00; A01P 3/00; C12N 1/205; C12R 2001/01
See application file for complete search history.

(56) References Cited

FOREIGN PATENT DOCUMENTS

| | | |
|---|---|---|
| CN | 114107132 A | 3/2022 |
| CN | 115612649 A | 1/2023 |
| CN | 116348589 A | 6/2023 |
| CN | 119020198 A | 11/2024 |
| WO | 2023240910 A1 | 12/2023 |

OTHER PUBLICATIONS

UnitJuggler "Converting mu to square Meters", 4 pages https://www.unitjuggler.com/convert-area-from-mu-to-m2.html Accessed Dec. 5, 2025 (Year: 2025).*
Title:Practical Manual for Diagnosis and Control of Vegetable Diseases and Pests, 1st Edition Publication Date: Jan. 31, 2012 Author Name and Publisher Name: Li Huiming et al., Shanghai Scientific and Technical Publishers Relevant Pages: p. 482.
Title:Plant Disease Research and Control, 1st Edition Publication Date: Mar. 31, 1998 Author Name and Publisher Name: Liu Yi, China Agricultural Science and Technology Press Relevant Pages: p. 650.
Title:Acta Agriculturae Boreali-Sinica, vol. 35, No. 3 Publication Date: Dec. 31, 2020 Author Name and Publisher Name: Liu Kun'ang et al., Screening and Identification of Bacillus Antagonistic Against Botrytis cinerea and Study on the Antibacterial Effect of Its Metabolites Relevant Pages: pp. 200-207.
Title: OMICS A Journal of Integrative Biology, vol. 20, No. 4 Publication Date: Dec. 31, 2016 Author Name and Publisher Name: Saber Khelaifia et al., "Microbial Culturomics to Map Halophilic Bacterium in Human Gut: Genome Sequence and Description of *Oceanobacillus jeddahense* sp. nov." Relevant Pages: pp. 248-258.

* cited by examiner

*Primary Examiner* — Thane Underdahl

(57) ABSTRACT

The invention relates to an *Oceanobacillus jeddahense* strain HMF12, preservation number CGMCC No. 30478. The microbial inoculant contains $4×10^9$ cfu/g to $7×10^9$ cfu/g of *Oceanobacillus jeddahense* HMF12 spores. This strain can promote seed germination and plant growth under salt stress conditions and effectively prevent and control crop diseases, especially strawberry gray mold.

4 Claims, 2 Drawing Sheets

Specification includes a Sequence Listing.

SEQUENCE LISTING

```
Sequence total quantity: 1
SEQ ID NO: 1              moltype = DNA   length = 828
FEATURE                  Location/Qualifiers
source                   1..828
                         mol_type = other DNA
                         organism = synthetic construct
SEQUENCE: 1
ggaaaaattc actatctttc tttccataaa ggggttcctg acggtgagat tgagattatt   60
ggggatacag atattacagg aaccgtaaca cactttatac cagatccgga aattttcaca  120
gaaactaccg aatatgatta tggaacatta gaacaacgtc tgagagagct tgctttctta  180
aataaaggat tgcgtatatc cattgaagat aaacgtacgg ataaagatcc ggcaacgtat  240
tattatgagg gcggaatcag ttcttatgta gaattcatta ataaaaataa agaagtactg  300
cacgaaccat tctatgctga aggggaagat cagggaattt ctgtagaggt tgctatccag  360
tataacgatg gatttgcgac cagcttatat tcttttgcta ataatattca tacctatgaa  420
ggcggaacac atgaagttgg tttccgttca gggctgacgc gtgcaatcaa tgattatgca  480
aaaaagaaca gcttattgaa agataatgaa tcaaacctgt ctggagagga tgtccgggaa  540
ggcttgacag caattgtttc cgtgaagcat ccagatccgc aatttgaggg acagacgaaa  600
acaaaactgg gaaatagcga agtacgtgca attacagatg gtgtattttc agagactttc  660
tctaaatttc tttacgaaaa tccaacgacc gcaaaaatta ttgtagaaaa agggttaatg  720
gcgtccagag cacgtttggc tgctaaaaaa gcaagagagc tgacacgtcg taaaagtgcg  780
ctcgatgtaa caagtctgcc aggaaaatta gctgattgtc tccaaaga               828
```

*OCEANOBACILLUS JEDDAHENSE* STRAIN HMF12 AND ITS APPLICATION

TECHNICAL FIELD

The invention relates to the field of agricultural microbial technology, specifically to an *Oceanobacillus jeddahense* strain HMF12 and its application.

STATEMENT REGARDING SEQUENCE LISTING

The sequence listing associated with this application is provided in text format in lieu of a paper copy and is hereby incorporated by reference into the specification. The name of the XML file containing the sequence listing is 25075TBYX-USP1-SL.xml. The XML file is 2,765 bytes; is created on Nov. 4, 2025; and is being submitted electronically via patent center.

BACKGROUND ART

Soil salinization and frequent plant diseases have long constrained the development of sustainable agriculture. Excessive soil salinity affects almost all life processes of plants, such as photosynthesis, protein synthesis, energy metabolism, and lipid metabolism, while also inhibiting plant growth and affecting seed germination and seedling emergence.

Gray mold, caused by *Botrytis cinerea*, frequently occurs in greenhouse-cultivated cucumbers, tomatoes, eggplants, sweet peppers, and strawberries. *Botrytis cinerea* is a globally distributed fungus that overwinters in the soil as sclerotia, conidia, or mycelia within diseased plant residues. Its hosts are mostly dicotyledonous plants. It primarily invades hosts through wounds, natural openings, and young tissues. After infection, it produces large quantities of conidia that spread via wind and rain for multiple reinfections, causing gray mold. Flowers, fruits, leaves, and stems can all be affected, leading to crop wilting and death, impacting yield and quality. It is one of the most difficult-to-control important diseases in production.

Therefore, finding a microorganism that can effectively prevent and control crop diseases while also enhancing seed germination rates or promoting plant growth under salt stress conditions is a primary direction for achieving biological control.

SUMMARY OF THE INVENTION

The purpose of the invention is to provide an *Oceanobacillus jeddahense* strain HMF12 and its application, which promotes plant seed germination and growth under salt stress conditions and effectively prevents and controls crop diseases, especially strawberry gray mold.

The invention adopts the following technical solutions.

An *Oceanobacillus jeddahense* strain HMF12, preserved under preservation number CGMCC No. 30478 at the China General Microbiological Culture Collection Center (CGMCC), located in Beijing, China, with a preservation date of Apr. 30, 2024.

The deposits were made and accepted under the Budapest Treaty and applicant avers under 37 CFR § 1.808(a) that the deposit was made under conditions that assure that:

(1) Access to the deposit will be available during pendency of the patent application making reference to the deposit to one determined by the Director to be entitled thereto under § 1.14 and 35 U.S. C. § 122, and (2) Subject to paragraph (b) of this section, all restrictions imposed by the depositor on the availability to the public of the deposited material will be irrevocably removed upon the granting of the patent.

Further, the *Oceanobacillus jeddahense* strain HMF12 can antagonize *Botrytis cinerea*.

Further, the *Oceanobacillus jeddahense* strain HMF12 is salt-alkali tolerant.

A microbial inoculant, wherein it comprises the above *Oceanobacillus jeddahense* strain HMF12.

Further, the microbial inoculant contains 4×109 cfu/g to 7×109 cfu/g of *Oceanobacillus jeddahense* strain HMF12 spores per gram.

An application of the *Oceanobacillus jeddahense* strain HMF12 for promoting plant seed germination under salt stress conditions.

An application of the *Oceanobacillus jeddahense* strain HMF12 for promoting plant growth under salt stress conditions.

An application of the *Oceanobacillus jeddahense* strain HMF12 for preventing and controlling crop gray mold.

The beneficial effects of the invention are as follows: the *Oceanobacillus jeddahense* strain HMF12 according to the invention has strong salt-alkali tolerance and high colonization rate in saline-alkali soil. The microbial inoculant prepared using this strain can improve crop emergence rates under saline-alkali soil conditions, promote crop growth, and prevent and control crop gray mold caused by *Botrytis cinerea*, achieving a control efficacy of 86.45% against strawberry gray mold.

BRIEF DESCRIPTION OF ACCOMPANY DRAWINGS

SPECIFIC EMBODIMENT OF THE INVENTION

Figure 1:
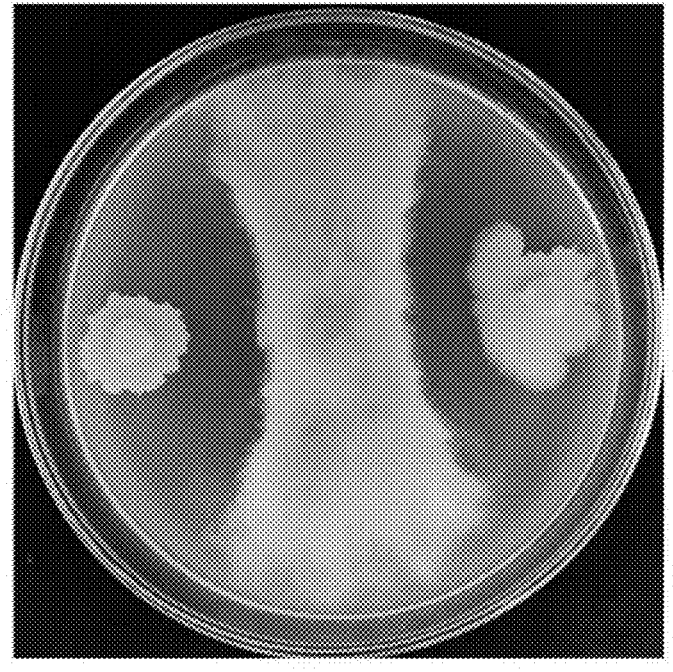
FIG. 1 shows the confrontation culture results of strain HMF12 and *Botrytis cinerea* according to the invention.

The invention will be further described hereinafter with reference to embodiments and drawings, and the protection scope of the invention is not limited thereto. Any modifications made by those skilled in the art within the scope defined by the claims also fall within the protection scope of the invention.

Experimental methods in the following embodiments are conventional methods unless otherwise specified. Reagents used in the following embodiments are conventional biochemical reagents purchased unless otherwise specified.

Embodiment 1: Isolation, Purification, and Screening of Strains

Six soil samples (100 g each) were collected from saline-alkali land in Huanghua City, Hebei Province. The collected soil samples were uniformly mixed. 10 g of the mixed soil was added to 100 mL of distilled water and stirred evenly. After standing for 1 minute, 1 mL of the supernatant was taken and added to a test tube containing 9 mL of sterile water to obtain a $1\times10^{-1}$ dilution. Serial dilutions were performed to obtain concentrations of $1\times10^{-4}$, $1\times10^{-5}$, and $1\times10^{-6}$. 0.1 mL of the diluted soil solution from each dilution ($1\times10^{-4}$, $1\times10^{-5}$, $1\times10^{-6}$) was spread onto a high-salt-alkali selective medium plate, spread evenly, and then incubated at 37° C. for 24-48 hours. Based on differences in colony and cell morphology, different strains were transferred to preservation medium slants, cultured at 37° C. for 1-2 days, and stored at 4° C. after full growth. A total of 24 salt-alkali tolerant strains were screened and numbered 01-24.

Formula of the high-salt-alkali selective medium: Peptone 10 g, Yeast extract 5 g, Composite inorganic salts (NaCl: KCl:MgCl$_2$=10:1:1) 30 g, Agar 20 g, Distilled water 1000 mL, pH 9.0, sterilized at 121° C. for 20 minutes.

Formula of the preservation medium: Peptone 10 g, Yeast powder 5 g, NaCl 10 g, Agar 20 g, Distilled water 1000 mL, pH 7.0, sterilized at 121° C. for 20 minutes.

Confrontation culture test: the 24 numbered strains, activated on LB solid medium, were inoculated on both sides of a PDA medium plate. An activated *Botrytis cinerea* plug (diameter 5 mm) was inoculated in the center of the medium. A PDA plate inoculated only with the pathogen served as the control. Plates were placed in a 28° C. incubator for 96 hours. When the control plate was fully covered with the pathogen, the antagonistic effect of the 24 strains against *Botrytis cinerea* was observed, and strains showing inhibition zones were selected for re-screening. Three strains numbered 04, 12, 17 showing antagonism against *Botrytis cinerea* were initially screened from the 24 strains.

Using *Botrytis cinerea* as the indicator fungus, the selected strains 04, 12, 17 were point-inoculated at four corners 3 cm from the center of the plate. A 5 mm activated *Botrytis cinerea* plug was simultaneously inoculated in the center. Each strain was tested in triplicate. Plates were incubated at 28° C. for 5 days. The diameter of the inhibition zone was measured, and the average inhibition rate was calculated. Strain 04 showed the strongest antagonism against *Botrytis cinerea*. The confrontation culture result is shown in FIG. 1. The *Botrytis cinerea* strain used was provided by the Institute of Biology, Hebei Academy of Sciences.

Considering the growth rate on high-salt medium and the antagonistic ability against *Botrytis cinerea* exhibited by the 24 screened salt-alkali tolerant strains, one strain, numbered 04, was selected. This strain showed strong antagonism against *Botrytis cinerea* and a high growth rate on the high-salt-alkali selective medium plate. It was named HMF12.

Embodiment 2: Identification of Strain HMF12

1. Morphological Identification

Figure 2:
FIG. 2 shows the colony morphology of *Oceanobacillus jeddahense* strain HMF12 according to the invention.
Figure 3:
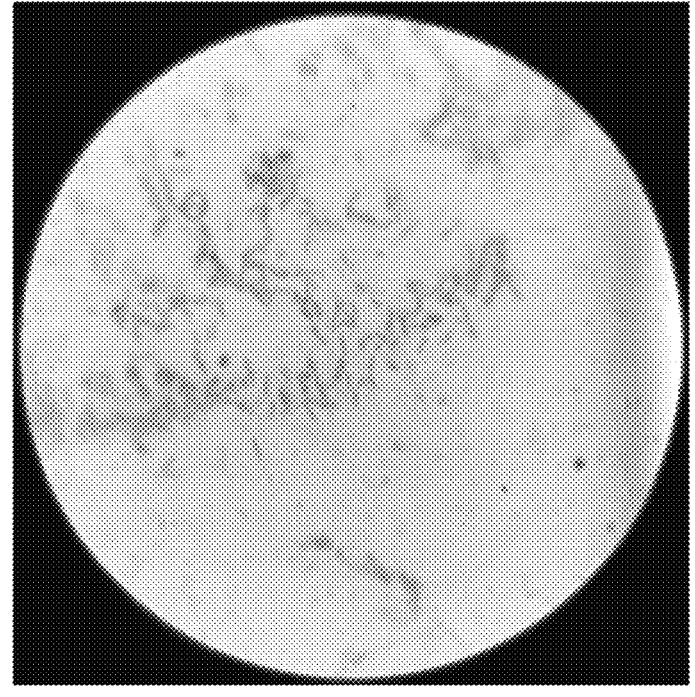
FIG. 3 shows the cell morphology of *Oceanobacillus jeddahense* strain HMF12 according to the invention.

Observation of colony morphology showed that HMF12 colonies (FIG. 2) are circular, with neat edges, and creamy white on Gibson medium. Microscopic observation revealed that HMF12 is Gram-positive, as shown in FIG. 3. Preliminary determination indicated that strain HMF12 is a *bacillus*.

2. Physiological and Biochemical Identification

Physiological and biochemical tests were performed on strain HMF12 following *Bergey's Manual of Determinative Bacteriology* and the *Common Bacterial System Identification Manual* by Dong Xiuzhu and Cai Miaoying. Results are shown in Table 1. Combined with morphological observations, HMF12 was preliminarily identified as a *Bacillus* strain.

TABLE 1

Physiological and Biochemical Characteristics of Strain HMF12

| Item | Result | Item | Result |
|---|---|---|---|
| M.R Test | + | Sucrose | + |
| V.P Test | + | Glucose | + |
| Aerobic Test | + | Fructose | + |
| Gelatin Test | + | Mannitol | − |

TABLE 1-continued

Physiological and Biochemical Characteristics of Strain HMF12

| Item | Result | Item | Result |
|---|---|---|---|
| Starch Hydrolysis | + | Starch | − |
| Gram Staining | + | Xylitol | − |
| Catalase Test | + | Maltose | + |
| 10% NaCl | + | Indole Reaction | − |

Note:
"+" indicates positive reaction; "−" indicates negative reaction.

3. Molecular Biological Identification

Figure 4:
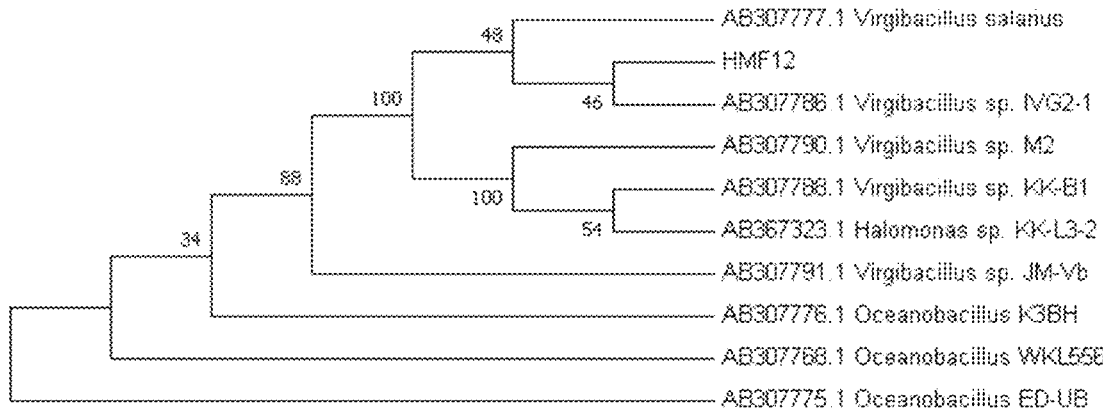
FIG. 4 shows the phylogenetic tree of *Oceanobacillus jeddahense* strain HMF12 based on 16S rDNA according to the invention, and 16S rDNA sequence of the *Oceanobacillus jeddahense* strain HMF12 is SEQ ID NO: 1.

DNA was extracted from strain HMF12. After PCR confirmation, the 16S rRNA gene was sequenced. The sequence was compared using BLAST on the NCBI website, and a phylogenetic tree was constructed (FIG. 4). Based on the phylogenetic tree results, combined with morphological observation and physiological-biochemical tests, the antagonistic strain HMF12 was identified as *Oceanobacillus jeddahense*.

Strain HMF12 was preserved at the China General Microbiological Culture Collection Center (CGMCC), located at Institute of Microbiology, Chinese Academy of Sciences, No. 1 West Beichen Road, Chaoyang District, Beijing, under preservation number CGMCC No. 30478, with a preservation date of Apr. 30, 2024.

Embodiment 3: Colonization Ability of *Oceanobacillus jeddahense* Strain HMF12

Three bacterial strains (HM-1, HM-3, HM-6) previously used by the applicant in production with good performance were selected for comparison. Colonization ability was evaluated using pot experiments.

(1) Soil for pot experiments: sterile soil 1 was taken from the applicant's experimental base (cinnamon soil), air-dried, and sterilized by high-temperature treatment. Saline-alkali soil for pot experiments was taken from saline-alkali land in Huanghua City, Hebei Province. Soil salinity was 0.31%. It was air-dried and sterilized by high-temperature treatment to make sterile soil 2.

(2) Strains HM-1, HM-3, HM-6, and HMF12 were inoculated into LB liquid medium, cultured at 30° C., 160 rpm for 48 hours to obtain fermentation broth. The broth was diluted to a bacterial suspension containing $1.0 \times 10^9$ CFU/mL.

(3) Sterile soil 1 and sterile soil 2 were uniformly mixed with solid fermentation medium at a ratio of 4:1 and placed in pots (diameter 10 cm, height 11 cm).

(4) 200 mL of the prepared bacterial suspension was applied by drenching. Pots were placed in trays filled with water, allowing water to be absorbed upwards through the bottom holes until the surface soil was moist. Trays were emptied, and pots were placed in a greenhouse at 20-28° C. After 15 days, 1 g soil samples were taken from a depth of 6 cm to detect viable bacteria count. Each strain had 5 replicates. Watering was done every 4 days.

Solid fermentation medium: wheat bran:rice husk:3% Glucose solution=7:3:3, Urea 2.16%, KH$_2$PO$_4$ 2.77%, mixed evenly, bagged, and sterilized at 121° C. for 60 minutes (intermittent sterilization twice).

The colonization number per gram of soil and colonization rate were detected for each strain, as shown in Table 2.

Colonization rate (%) = (Colonization number/Inoculation number) × 100.

TABLE 2

Detection Results of Strain Colonization Rate

| | Strain | Inoculation Number (CFU/g soil) | Colonization Number (CFU/g soil) | Colonization Rate (%) |
|---|---|---|---|---|
| Sterile | HM-1 | $1.0 \times 10^9$ | $1.56 \times 10^9$ | 156 |
| Soil 1 | HM-3 | $1.0 \times 10^9$ | $1.45 \times 10^9$ | 145 |
| | HM-6 | $1.0 \times 10^9$ | $1.46 \times 10^9$ | 146 |
| | HMF12 | $1.0 \times 10^9$ | $1.64 \times 10^9$ | 164 |
| Sterile | HM-1 | $1.0 \times 10^9$ | $0.76 \times 10^9$ | 76 |
| Soil 2 | HM-3 | $1.0 \times 10^9$ | $0.84 \times 10^9$ | 84 |
| | HM-6 | $1.0 \times 10^9$ | $1.12 \times 10^9$ | 112 |
| | HMF12 | $1.0 \times 10^9$ | $1.54 \times 10^9$ | 154 |

As shown in Table 2, *Oceanobacillus jeddahense* strain HMF12 has better colonization ability compared to the other control strains. In cinnamon soil, the colonization number of HMF12 was $11.64 \times 10^9$ CFU/g soil. In saline-alkali soil, it was $1.54 \times 10^9$ CFU/g soil. The small difference indicates that saline-alkali soil has minimal impact on the colonization of HMF12. This strain can colonize and grow well in saline-alkali land.

Embodiment 4: Growth-Promoting Effect of *Oceanobacillus jeddahense* Strain HMF12 on Wheat Germination Strain HMF12 was inoculated into LB liquid medium, cultured at 30° C., 160 rpm for 48 hours to obtain fermentation broth. The broth was diluted to a bacterial suspension containing $1.0 \times 10^9$ CFU/mL.

The prepared bacterial suspension was diluted with sterile water at volume ratios of 1:0, 1:10, 1:20, 1:30, 1:40, 1:50, and 0:1, designated as T0, T1, T2, T3, T4, T5, and CK, respectively (7 treatments). Wheat seeds (drought-salt-tolerant variety 'Jiemai 19') were disinfected with 75% ethanol for 3 minutes, then with 1% sodium hypochlorite for 10-15 minutes. Seeds were soaked in different concentrations of the bacterial suspension for 24 hours. Two layers of filter paper were placed in Petri dishes, moistened with 15 mL sterile water, and placed in a 28° C. incubator. Seed germination rates were measured after 24 hours, and on days 3, 5, and 7.

TABLE 3

Effect of Diluted *Oceanobacillus jeddahense* Strain HMF12 Fermentation Broth on Wheat Seed Germination Rate

| Treatment | Germination Rate on Day 1 (%) | Germination Rate on Day 3 (%) | Germination Rate on Day 5 (%) | Germination Rate on Day 7 (%) |
|---|---|---|---|---|
| T0 | 67 | 76 | 78 | 81 |
| T1 | 64 | 85 | 87 | 89 |
| T2 | 67 | 86 | 94 | 96 |
| T3 | 80 | 87 | 95 | 97 |
| T4 | 66 | 73 | 80 | 84 |
| T5 | 63 | 72 | 76 | 83 |
| CK | 62 | 63 | 75 | 77 |

As shown in Table 3, the HMF12 fermentation broth has a certain promoting effect on wheat seed germination. Without dilution, the germination rate of soaked wheat seeds reached 81.0% on day 7, a 4% increase over the control. As the dilution ratio increased, the germination rate showed different changes. When the broth was diluted 20 times and 30 times, the germination rates reached 96% and 97%, respectively, representing increases of 19% and 20% compared to the control's 77%.

Embodiment 5: Growth-Promoting Effect of *Oceanobacillus jeddahense* Strain HMF12 on Wheat Germination Under Salt Stress 1) Preparation of Bacterial Suspension: a loopful of HMF12 from the preservation medium was inoculated onto an LB solid plate and activated at 30° C. for 48 hours. After single colonies appeared, a single colony was picked using a 100 μL yellow pipette tip and placed into a 100 ml conical flask containing 30 mL LB liquid medium. It was cultured at 30° C., 180 rpm for 72 hours to obtain HMF12 fermentation broth. The broth was diluted with sterile distilled water, and the optical density (OD) of the suspension was adjusted to 0.5 at 600 nm wavelength using a spectrophotometer. It was set aside for later use.

2) Test Seeds Pre-Treatment: the test material was wheat variety 'Nongda 212' seeds purchased from a local seed company. Uniform-sized wheat seeds were selected, surface-sterilized with 0.1% mercuric chloride for 3 minutes, rinsed 3 times with sterile distilled water, and soaked at room temperature for 2 hours in sterile water (CK) or the prepared bacterial suspension (HMF12). After soaking, seeds were rinsed 2-3 times with distilled water and placed neatly in Petri dishes (with two layers of moist sterile filter paper at the bottom), 20 seeds per dish. Each group had 5 replicates. Seeds were irrigated with 0%, 0.4% (low salt), or 0.8% (high salt) NaCl solution and placed in a growth chamber. The light/dark cycle was 12 hours/12 hours, day/night temperature was 28° C./23° C., and relative humidity was 70%.

Germination was observed and recorded daily starting from day 1 of salt stress. A seed was considered germinated when the radicle length reached half the seed length. The number of seeds germinated by day 7 was recorded as the final germination number. Germination rate (%) was calculated as (final germination number/total seeds tested)×100. Test results are shown in Table 4.

TABLE 4

Germination Rate of Wheat Seeds Soaked in *Oceanobacillus jeddahense* Strain HMF12 Fermentation Broth under Different Salt Stresses

| Seed Soaking Treatment | Salt Concentration (%) | Germination Rate (%) |
|---|---|---|
| CK (After Soaking 2 Hours in Sterile Water) | 0 | 81 |
| | 0.4 | 36 |
| | 0.8 | 14 |
| HMF12 (After Soaking 2 Hours) | 0 | 96 |
| | 0.4 | 65 |
| | 0.8 | 36 |

From Table 4, it can be seen that under salt stress, the germination rate of wheat seeds soaked in HMF12 suspension was higher than those soaked in sterile water by 15% (0% salt), 29% (0.4% salt), and 22% (0.8% salt). This indicates that HMF12 soaking can alleviate salt stress damage to some extent, and the effect is better under low salt (0.4%) stress than under high salt (0.8%) stress.

Embodiment 6: Promotion of Corn Plant Growth by *Oceanobacillus jeddahense* Strain HMF12

A corn pot experiment was conducted to evaluate the growth-promoting effect of *Oceanobacillus jeddahense* Strain HMF12 on corn plants. Potting soil was a 1:1 mixture of loam soil from Changli County and coastal saline-alkali soil from Changli, with a measured salinity of 0.33%. The pot experiment included a CK group (no HMF12 fermentation broth) and a fermentation broth group (with HMF12 fermentation broth). Each treatment had 15 corn seedlings, 3 seedlings per pot (5 pots total). Pots (inner diameter 12.5 cm, height 11.5 cm) were filled with 0.9 kg of soil. When corn seedlings reached the 3-leaf stage, uniform seedlings were selected for transplanting. The fermentation broth group received HMF12 fermentation broth ($1.0\times10^9$ CFU/mL) applied near the roots at transplanting. After adding the HMF12 suspension, the final inoculation amount was $5.2\times 10^6$ CFU/g soil. The CK group received an equal amount of sterile saline solution as control. A second application was performed 7 days later, adding the same amount of bacterial suspension/saline to the pot soil. Plant indicators were measured at the jointing stage (fastest growth period). Corn plants treated with strain HMF12 showed significant growth differences compared to the CK group.

Plant height, stem diameter, and root dry weight for all plants in each treatment were measured, as shown in Table 5. Results showed that plant height, root dry weight, and leaf dry weight of HMF12-treated corn plants increased by 35.59%, 83.44%, and 80.50%, respectively, compared to CK. This indicates that *Oceanobacillus jeddahense* Strain HMF12 can significantly promote corn plant growth under saline-alkali soil conditions.

TABLE 5

Measurement Results of Plant Height and Biomass of Corn Plants at Jointing Stage under Different Treatments

| Treatment | Plant Height (cm) | Root Dry Weight (g/plant) | Leaf Dry Weight (g/plant) |
|---|---|---|---|
| CK Group | 101.45 | 6.22 | 26.47 |
| Fermentation Broth Group | 137.56 | 11.41 | 47.78 |

Embodiment 7: Field Application of *Oceanobacillus jeddahense* Strain HMF12 Inoculant in Strawberry Cultivation The *Oceanobacillus jeddahense* HMF12 strain was inoculated into a 30 L fermenter containing 15 L PB liquid medium and cultured at 28° C., 180 rpm for 36 hours. Spores were obtained by centrifugation, then spray-dried. Soluble starch was mixed with the spore powder to form a spore preparation with a final concentration of $4\times10^9$ cfu/g to $7\times10^9$ cfu/g.

Field trials of the *Bacillus* agent against gray mold were conducted in continuous cropping strawberry greenhouses in Changli County and Funing District, Hebei Province. During the early flowering stage and initial fruiting stage, the spore preparation was sprayed twice onto plant leaves and/or young strawberry fruits after suspending in water at a weight ratio of 1:300. Gray mold incidence was investigated seven days after the second spray. The application rate was 100 grams of spore preparation per mu (approximately 667 m$^2$) (final spray concentration: $1.62\times10^7$ cfu/ml). Carbendazim is an effective agent for controlling strawberry gray mold. The conventional control used 25% carbendazim wettable powder diluted 300 times, sprayed twice during the early flowering and initial fruiting stages. The blank control received no control agent but the same weight of water as the experimental groups. Each treatment had three replicates. Strawberry gray mold incidence was investigated.

Investigation method: at the ripening stage, a diagonal five-point sampling method was used. Twenty plants were fixed at each point (100 plants total) to investigate disease incidence and disease index. Total plants investigated and diseased plants were recorded.

Grading standard for strawberry gray mold disease index:

0 level: No symptoms;

1 level: Lesion area accounts for less than or equal to 5% of the whole fruit surface;

3 level: Lesion area accounts for 6%-10% of the whole fruit surface;

5 level: Lesion area accounts for 11%-25% of the whole fruit surface;

7 level: Lesion area accounts for 26%-50% of the whole fruit surface;

9 level: Lesion area accounts for greater than 50% of the whole fruit surface.

Control Efficacy Calculation Method:

Disease incidence (%) =

(Total diseased plants/Total plants investingated) × 100%;

Diseased index (%) = [∑(Number of diseased plants × Diseased level value)]/

(Total plants investigated × Highest level value) × 100;

Control efficacy (%) = [(Disease index of control area − Disease index of treatment area)/

Disease index of control area] × 100.

The control efficacy is shown in Table 6. Using this *Bacillus* agent can reduce strawberry gray mold incidence and disease index, achieving over 94.71% control efficacy after just 7 days.

TABLE 6

Control Efficacy of *Oceanobacillus jeddahense* Strain HMF12 Inoculant against Strawberry Gray Mold

| Test Site | Treatment | Disease Incidence (%) | Disease Index (%) | Control Efficacy (%) |
|---|---|---|---|---|
| Changli | Blank Control | 72 | 63.45 | — |
| | Conventional Control | 23 | 19.40 | 69.42 |
| | HMF12 Spore Preparation | 5 | 3.25 | 94.87 |
| Funing | Blank Control | 74 | 62.40 | — |
| | Conventional Control | 23 | 20.20 | 67.63 |
| | HMF12 Spore Preparation | 6 | 3.30 | 94.71 |

From the above results, it can be seen that strain HMF12 according to the invention has good antagonism against strawberry gray mold. Its spore preparation can effectively prevent and control the occurrence of gray mold in strawberry greenhouses, and its efficacy is superior to that of carbendazim.

The above are only preferred embodiments of the invention and are not intended to limit the scope of protection. Any improvements made to the invention by those skilled in the art without creative effort should be considered within the protection scope of the invention.

The invention claimed is:

1. An application method of *Oceanobacillus jeddahense* strain HMF12, comprising inoculating the *Oceanobacillus jeddahense* strain HMF 12 into a fermenter containing a Peptone Broth (PB) liquid medium to obtain spores to thereby prepare a spore preparation;

suspending the spore preparation in water to obtain an *Oceanobacillus jeddahense* strain HMF12 inoculant;

spraying the *Oceanobacillus jeddahense* strain HMF 12 inoculant onto at least one of leaves and young fruits of strawberry plants during an early flowering stage and an initial fruiting stage at a preset application rate, so as to prevent and control strawberry gray mold of the strawberry plants;

wherein the *Oceanobacillus jeddahense* strain HMF12 has been deposited under the preservation number CGMCC No. 30478.

2. The application method as claimed in claim 1, wherein the spore preparation has a final concentration of $4 \times 10^9$ colony forming units per gram (cfu/g) to $7 \times 10^9$ cfu/g.

3. The application method as claimed in claim 1, wherein the weight ratio of the spore preparation in water is 1:300.

4. The application method as claimed in claim 1, wherein the preset application rate is 100 grams of the *Oceanobacillus jeddahense* strain HMF12 inoculant per mu.

* * * * *